(12) United States Patent
Chung

(10) Patent No.: US 9,296,987 B2
(45) Date of Patent: Mar. 29, 2016

(54) MULTI-COATED LACTIC ACID BACTERIA AND PREPARING METHOD THEREOF

(75) Inventor: Myung Jun Chung, Seoul (KR)

(73) Assignee: Cell Biotech Co., Ltd., Gyeonggi-do (KR)

( * ) Notice: Subject to any disclaimer, the term of this patent is extended or adjusted under 35 U.S.C. 154(b) by 308 days.

(21) Appl. No.: 13/519,540

(22) PCT Filed: Oct. 11, 2011

(86) PCT No.: PCT/KR2011/007535
§ 371 (c)(1),
(2), (4) Date: Jun. 27, 2012

(87) PCT Pub. No.: WO2012/060554
PCT Pub. Date: May 10, 2012

(65) Prior Publication Data
US 2012/0282304 A1    Nov. 8, 2012

(30) Foreign Application Priority Data

Nov. 2, 2010 (KR) .......................... 10-2010-0107929
Sep. 15, 2011 (KR) .......................... 10-2011-0093074

(51) Int. Cl.
| | |
|---|---|
| C12N 1/20 | (2006.01) |
| C12N 1/00 | (2006.01) |
| A23C 9/13 | (2006.01) |
| A23C 9/123 | (2006.01) |
| A23L 1/30 | (2006.01) |
| A23L 1/03 | (2006.01) |
| A61K 35/744 | (2015.01) |
| A61K 35/747 | (2015.01) |
| A23C 11/10 | (2006.01) |
| C12N 1/04 | (2006.01) |

(52) U.S. Cl.
CPC ................ *C12N 1/20* (2013.01); *A23C 9/1234* (2013.01); *A23C 9/1238* (2013.01); *A23C 11/106* (2013.01); *A23L 1/0345* (2013.01); *A23L 1/3014* (2013.01); *A61K 35/744* (2013.01); *A61K 35/747* (2013.01); *C12N 1/04* (2013.01); *A23V 2002/00* (2013.01)

(58) Field of Classification Search
None
See application file for complete search history.

(56) References Cited

FOREIGN PATENT DOCUMENTS

| JP | 04364123 | 12/1992 |
|---|---|---|
| KR | 10-2002-0069863 | 9/2002 |
| KR | 10-2003-0070799 | * 9/2003 |
| KR | 10-2009-0082305 | 7/2009 |
| WO | 2009093785 | * 7/2009 |

OTHER PUBLICATIONS

Cha et al. (Biotechnol & Biotechol. E1. 2011, 25 (3): 2489-2493).*
International Search Report, Application No. PCT/KR2011/007535, dated May 21, 2012.

* cited by examiner

*Primary Examiner* — Jennifer Graser
(74) *Attorney, Agent, or Firm* — Nixon Peabody LLP

(57) ABSTRACT

The present invention relates to multi-coated lactic acid bacteria coated with a multi-coating layer forming bacterial clusters and including protein, polysaccharide, and edible oil/fat component, and a preparing method thereof. The multi-coated lactic acid bacteria according to the present invention may achieve an improved acid resistance, a bile resistance, and an accelerated test stability, may have a low moisture content to be particularly stable against a moisture variation, and thus may be appropriately used to prepare various products including lactic acid bacteria.

11 Claims, No Drawings

MULTI-COATED LACTIC ACID BACTERIA AND PREPARING METHOD THEREOF

CROSS-REFERENCE TO RELATED APPLICATIONS

This application is a U.S. national stage of International Patent Application No. PCT/KR2011/007535, filed Oct. 11, 2011, which claims priority to Korean Patent Application No. 10-2011-0093074 filed Sep. 15, 2011 and Korean Patent Application No. 10-2010-0107929 filed Nov. 2, 2010, the contents of which are each incorporated herein by reference in its entirety.

TECHNICAL FIELD

The present invention relates to multi-coated lactic acid bacteria, and more particularly, to multi-coated lactic acid bacteria coated with a multi-coating layer forming bacterial clusters and including protein, polysaccharide, and edible oil/fat component so as to achieve an improved acid resistance, a high bile resistance, and a high accelerated test stability, and to have a low moisture content to be particularly stable against a moisture variation, and a preparing method thereof.

BACKGROUND ART

The lactic acid bacteria live in the intestines of mammals and prevent abnormal fermentation by saprophytes. Thus, they are utilized as medicine for intestinal disorders. For example, *L. bulgaricus* is the lactic acid bacteria that have been known from long ago. It is used for the production of yogurt and also as a starter when producing cheese or cultured butter. And, the aerobic lactic acid bacteria *L. acidophilus*, which is found in the intestines of all mammals including human and other animals, is used for the production of butter or milk or for the treatment of autointoxication. Meanwhile, *L. lactis* produces d- and l-lactic acids. It is used for the production of butter or cheese, and is the most important lactic acid bacteria for dairying. In addition, *lactobacillus bifidus* is also well known. A large number of *lactobacillus bifidus* is found particularly in the intestines of breast-fed infants, and the number is gradually reduced while the infants grow. As such, it is regarded as being important for the health in early childhood. Also, like the other lactic acid bacteria, its fermentation product generates organic acid and antibacterial active materials to inhibit harmful intestinal bacteria. Currently, research is being actively conducted on lactic-acid fermented milk using *lactobacillus bifidus*, and products to be added to powdered formula to improve the health of formula-fed infants.

The lactic acid bacteria settle in the intestine and provide various physiological activities, including activation of intestinal movement, inhibition of harmful bacteria, promotion of synthesis of vitamins and immunostimulants, and the like. When orally taken, lactic acid bacteria tend to be killed by gastric acid or bile acid and do not exert their physiological activities.

In order to solve this problem, techniques for coating lactic acid bacteria have been developed. Conventional techniques for coating lactic acid bacteria include enteric-coated lactic acid bacteria using capsules and microencapsulated lactic acid bacteria using gelatin, sugar, gum, and the like.

Specifically, the conventional techniques for coating lactic acid bacteria are characterized by a separate coating process followed by collecting process of lactic acid bacteria. More specifically, the conventional lactic acid bacteria coating process is performed by adding an aqueous coating composition capable of forming ultrafine spherical beads to lactic acid bacteria powder, and performing stirring, mixing and freeze-drying.

Because the conventional techniques for coating lactic acid bacteria include collecting cultured lactic acid bacteria and making them into powder after drying, followed by mixing with a coating composition and stirring, they are associated with the following problems. The use of expensive coating agent and addition of the coating process result in increased production cost. Further, aseptic manipulation is difficult because other bacteria may be included. Besides, use of cryoprotectant and stabilizer during a freeze-drying process followed by coating process for ensuring superior viability and stability may result in interactions between materials or redundancy of processes.

In order to solve these problems, the present inventors have filed a patent related to a method for preparing double-coated lactic acid bacteria with improved bacterial stability and processing stability through prevention of direct interaction with air and moisture and through enhanced heat resistance, acid resistance and bile resistance have been developed (Korean Patent Application No. 2001-0010397) and a patent related to a method for preparing triple-coated lactic acid bacteria further improved from the double-coated lactic acid bacteria (Korean Patent Application No. 2008-0008267).

However, the above improved techniques for coating lactic acid bacteria may be appropriated used in powder-type products but may not sufficiently prevent killing of lactic acid bacteria by moisture in watery foods. Hence, they can be used only in restrictive fields against a broad range of foods.

Meanwhile, edible oils and fats are obtained from animals such as cows, pigs, and sheep and various oily seeds by using a refining method, a press method, or an extraction method using an organic solvent. Most edible oils and fats are hardly melted in water and alcohol and are melted well in an organic solvent such as ether or benzene. Also, their specific gravity is less than that of water. According to the type of fatty acid, if the content of an unsaturated fatty acid is high, it has a low melting point and is in a liquid state at room temperature. If the content of a saturated fatty acid is high, it has a high melting point and thus is in a solid state at room temperature. Due to the above characteristics, if lactic acid bacteria are coated with an edible oil/fat, they may prevent water contact to a certain level and may be used in various food groups.

However, due to difficulties of processing, any edible oil/fat has not been used as a coating agent of lactic acid bacteria.

As such, the present inventors have added an edible oil/fat as a coating agent of lactic acid bacteria conventionally coated with protein, polysaccharide, and nanoparticles so as to further improve heat resistance, acid resistance, and bile resistance of the lactic acid bacteria, and particularly to effectively increase stability against a moisture variation, thereby completing the present invention.

DISCLOSURE OF THE INVENTION

Technical Problem

The present invention provides multi-coated lactic acid bacteria coated with a multi-coating layer forming bacterial clusters and including protein, polysaccharide, and edible oil/fat component so as to achieve an excellent acid resistance, a bile resistance, and an accelerated test stability, and to have a low moisture content to be particularly stable against a moisture variation.

The present invention also provides a method of preparing the multi-coated lactic acid bacteria.

The present invention also provides a product including the multi-coated lactic acid bacteria.

Technical Solution

According to an aspect of the present invention, there is provided multi-coated lactic acid bacteria including a multi-coating layer forming bacterial clusters and including protein, polysaccharide, and edible oil/fat component; and lactic acid bacteria coated with the multi-coating layer.

The multi-coating layer may be formed by protease-processing an aqueous protein solution and fermenting lactic acid bacteria in the protease-processed aqueous protein solution so as to prepare a concentrated aqueous solution of lactic acid bacteria, and adding the polysaccharide and edible oil/fat component into the concentrated aqueous solution of lactic acid bacteria.

The multi-coating layer may further include a nanoparticle component.

The configuration of the present invention will now be described in detail.

The lactic acid bacteria may comprise at least one selected from the group consisting of genus *Streptococcus*, genus *Lactococcus*, genus *Enterococcus*, genus *Lactobacillus*, genus *Pediococcus*, genus *Leuconostoc*, genus *Weissella*, or genus *Bifidobacterium*.

The protein component may be formed by adding a sugar component for culturing lactic acid bacteria into a protease-processed aqueous protein solution including isolated soy protein and powdered skim milk solution, and fermenting the lactic acid bacteria in the protease-processed aqueous protein solution. An aqueous protein solution including soy peptone and casein peptone may be used instead of the protease-processed aqueous protein solution including isolated soy protein and powdered skim milk solution.

The sugar component for culturing lactic acid bacteria may include glucose, yeast extract, and an ionic component. In this case, the aqueous protein solution may be, but not limited to, 1 to 20% of an aqueous solution prepared by mixing isolated soy protein and powdered skim milk, and the protease may be, but not limited to, pepsin, trypsin, chymotrypsin, or elastase.

The sugar component such as the glucose, the yeast extract, and the ionic component is a component required for survival and growth when the lactic acid bacteria are fermented, and 1 to 5 weight % of the glucose, 0.1 to 1.5 weight % of the yeast extract, and 0.01 to 0.1 weight % of the ionic component may be added with respect to a total weight of the protease-processed aqueous protein solution.

The ionic component may be, but not limited to, ammonium citrate, sodium acetate, dipotassium phosphate, magnesium sulfate, manganese sulfate, or sodium chloride. The materials for culturing the lactic acid bacteria may be sterilized before the lactic acid bacteria are added.

Also, a concentrated aqueous solution of lactic acid bacteria in which lactic acid bacteria are coated with a protein component may be formed by performing a separating and concentrating process on the protease-processed and lactic acid bacteria-fermented aqueous protein solution. As such, the lactic acid bacteria may be concentrated to have a concentration of $10^{10}$ to $10^{11}$ CFU/Ml and protein remnants may be settled together with the bacteria to increase the efficiency of protein coating and to achieve effective coating. For example, after the lactic acid bacteria are fermented, the bacteria may be separated and concentrated by using a continuous centrifuge, and the settled protein remnants may be coated on the bacteria to form the protein component. The protein component provides a heat resistance, an acid resistance, and a bile resistance to the lactic acid bacteria.

The polysaccharide component may be added by adding an aqueous polysaccharide solution into the concentrated aqueous solution of lactic acid bacteria. In the aqueous polysaccharide solution, the polysaccharide component may have a concentration of 0.1 to 30%, and may be, but not limited to, selected from the group consisting of xantan gum, carboxymethyl cellulose (CMC), levan, and mixtures thereof.

The polysaccharide component may be added by 0.001 to 10 weight % with respect to a total weight of the concentrated aqueous solution of lactic acid bacteria including the protein component. Since the lactic acid bacteria are coated with the polysaccharide component, due to a strong adhesive force of the polysaccharide component, the bacteria may be combined to form bacterial clusters having a very dense structure. In particular, in the state of an aqueous solution, since the polysaccharide component has an extremely low solubility under an acidic condition and is easily dissociated and liquated above a neutral pH, the polysaccharide component improves stability and intestinal settlement of the lactic acid bacteria under an acidic condition.

In the present invention, the multi-coating layer may be formed by adding an edible oil/fat component into the concentrated aqueous solution of lactic acid bacteria together with the polysaccharide component. The edible oil/fat component may be animal or vegetable oil/fat, and solid edible oil/fat at room temperature may be appropriately used. Since the multi-coated lactic acid bacteria may be freeze-dried and powdered to use as a product, the edible oil/fat component that is emulsified by an emulsifier to be coated and then becomes solid (powder) at room temperature may be appropriately used. The edible oil/fat component may be, but not limited to, for example, selected from the group consisting of edible beef tallow, edible pork lard, coconut oil, palm oil, cocoa fat, and mixtures thereof, and more particularly, edible beef tallow and palm oil.

The edible oil/fat component may be emulsified and homogenized before being added into the concentrated aqueous solution of lactic acid bacteria. In this case, an edible emulsifier for emulsifying the edible oil/fat component may be lecithin, glycerin fatty acid ester, or sucrose fatty acid ester, and more particularly, lecithin separated from beans or egg yolks. The edible emulsifier may be added by 0.1 to 10 weight %, and more particularly, by 0.5 to 5 weight % with respect to a total weight of the edible oil/fat component. The homogenizing process may be performed by using a homogenizer. The edible oil/fat component may be added by 1 to 20 weight %, and more particularly, by 1 to 5 weight % with respect to a total weight of the concentrated aqueous solution of lactic acid bacteria.

Since the lactic acid bacteria are coated with the multi-coating layer including the edible oil/fat component, the lactic acid bacteria may have an increased resistance against external environmental stresses, and thus may have an improved acid resistance, a bile resistance, and a storage stability. Also, since the lactic acid bacteria are coated with a fatty component, the lactic acid bacteria may not react with moisture to have a low moisture content, and may have an improved stability against a moisture variation.

When the multi-coating layer is formed, the polysaccharide and edible oil/fat component may be added into the concentrated aqueous solution of lactic acid bacteria in the order of the polysaccharide component and the edible oil/fat component, in the order of the edible oil/fat component and the polysaccharide component, or simultaneously at the same time.

Alternatively, the multi-coating layer may further include a nanoparticle component. The nanoparticle component may be formed of, but not limited to, nanoparticles formed by using a material selected from the group consisting of gelatin, casein, lecithin, dextran, gum acacia, cholesterol, stearic acid, calcium stearate, sorbitan ester, phosphate, cellulose, polyvinylalcohol, and combinations thereof, and more particularly, of solid lipid nanoparticles formed by using, for example, stearic acid and soy lecithin. The nanoparticles may have a size of 50 to 300 nm, and more particularly, of 100 to 200 nm so as to be effectively coated on the lactic acid bacteria.

In order to partially separate the nanoparticles, filtration, microfiltration, centrifugation, ultracentrifugation, precipitation, decantation or a combination thereof may be added according to a common nanoparticle preparation method. Also, a process of destabilizing a suspension may be included. The destabilizing process may be performed before the filtration, microfiltration, centrifugation, ultracentrifugation, or precipitation process.

Specifically, the destabilizing process may include adding a destabilizing liquid into a suspension. The destabilizing liquid may be polar and may be mixed with a nonpolar liquid. The destabilizing liquid may be mixed with water. For example, the destabilizing liquid may be acetone, ethanol, methanol, or any other liquid.

The destabilizing process may include, for example, a process of changing the temperature of the suspension into an unstable temperature. Depending on situations, the temperature change can be accomplished by heating or cooling. Furthermore, a process of washing the nanoparticles may be included. The washing process may include contacting the nanoparticles with a washing liquid (aqueous or organic) and separating the nanoparticles from the washing liquid.

For example, a part of or the whole washing process may include suspending the nanoparticles in a washing liquid, stirring randomly collected washing liquid and laminated nanoparticles, and separating the nanoparticles from the washing liquid by using, for example, any separation method mentioned above. Alternatively, a part of or the whole washing process may include passing the washing liquid through the nanoparticles which may be held, for example, in a filter.

The washing may be performed due to phase separation using a decantation funnel. The aqueous washing liquid may be water or an aqueous liquid, for example, a salt solution. The organic washing liquid may be a solvent, which may be a polar or nonpolar solvent, for example, methanol, ethanol, isopropanol, acetone, dichloromethane, chloroform, ethyl acetate, toluene, any other solvent, or a combination thereof.

The washing process may include heating or cooling the suspension at about 10 to 70□. The heating or cooling temperature may be a temperature at which the status of a system is changed so that the formation of a stable phase by the system is prevented. Also, a solvent mixture may be used to change the status of the system and thus to prevent it from forming a stable single phase. Also, a process of fluidized-bed-drying the nanoparticles may be included, and the fluidized-bed-drying process may include heating the nanoparticles. For example, the heating temperature may be about 30 to 80□, and more particularly, 40 to 60□.

The drying process may include passing a gas with powder to be coated through nanoparticles. The gas may be an inactive gas to the nanoparticles, for example, air, nitrogen, argon, helium, carbon dioxide, or a mixture thereof. The drying process may include applying partial vacuum to the nanoparticles. The partial vacuum may have an is absolute pressure of, for example, about 0.01 to 0.5 atmosphere.

The nanoparticle component may be coated by using a well-known conventional nanoparticle coating method that does not reduce activities of the lactic acid bacteria, such as a physical coating method (a gas evaporation—condensation method, a mechanical synthesis method, a coating method, etc.) or a chemical coating method (a precipitation method, a spray drying method, a solid synthesis method, etc.). Preferably, the nanoparticle component added into the concentrated aqueous solution of lactic acid bacteria may be stirred together with the protein, polysaccharide, and edible oil/fat component such that the multi-coating layer is formed in the form of bacteria clusters in which the components included in the multi-coating layer are not divided into separate layers.

In the present invention, the nanoparticle component is coated on surfaces of the lactic acid bacteria so as to increase resistance against external environmental stresses and to increase a survival ratio of the lactic acid bacteria. The nanoparticle component may be used by 1 to 10 weight %, and more particularly, by 0.5 to 5 weight %, with respect to a total weight of the concentrated aqueous solution of lactic acid bacteria. The nanoparticle component may be added into the concentrated aqueous solution of lactic acid bacteria after the polysaccharide component is added. However, the order of adding the nanoparticle component is not limited thereto.

The above-described multi-coating layer may be formed in the form of bacteria clusters including the protein, polysaccharide, and edible oil/fat component, or including the protein, polysaccharide, nanoparticle, and edible oil/fat component. The bacteria clusters for forming the multi-coating layer are formed in a sort of matrix structure in which the components included in the multi-coating layer are mixed and are not divided into separate layers, and the lactic acid bacteria are coated with the multi-coating layer formed in bacteria clusters.

In the present invention, the lactic acid bacteria may be freeze-dried to further increase storage stability. For this, a cryoprotectant may be additionally added into the concentrated aqueous solution of lactic acid bacteria in addition to the polysaccharide, nanoparticle, and edible oil/fat component for forming the multi-coating layer. In this case, the cryoprotectant may be added after adding or together with the components for forming the multi-coating layer. Preferably, the cryoprotectant may be added first into the aqueous protein solution in which lactic acid bacteria are concentrated, and then the components for forming the multi-coating layer may be added.

Although a freeze-drying process according to a conventional method is performed after adding the cryoprotectant, the lactic acid bacteria are not killed during the freeze-drying process. The cryoprotectant may be trehalose, maltodextrin, starch, or powdered skim milk, and may be used in the state of an aqueous solution having a concentration of 1 to 50%. Also, the cryoprotectant may be added and used by 1 to 50 weight % with respect to a total weight of the concentrated aqueous solution of lactic acid bacteria.

According to another aspect of the present invention, there is provided a method of preparing multi-coated lactic acid bacteria, the method including the steps of: (a) forming a concentrated aqueous solution of lactic acid bacteria by adding a sugar component for culturing lactic acid bacteria into a protease-processed aqueous protein solution, and fermenting the lactic acid bacteria in the protease-processed aqueous protein solution; (b) adding polysaccharide and edible oil/fat component into the concentrated aqueous solution of lactic acid bacteria; and (c) freeze-drying the concentrated aqueous solution of lactic acid bacteria including the protein, polysaccharide, and edible oil/fat component.

The sugar component for culturing lactic acid bacteria in the step (a) may include glucose, yeast extract, and an ionic component. In the step (b), the polysaccharide and edible oil/fat component may be added sequentially in a certain order, or simultaneously at the same time.

The step (b) may include adding a nanoparticle component into the concentrated aqueous solution of lactic acid bacteria.

According to another aspect of the present invention, there is provided a product including the multi-coated lactic acid bacteria.

The multi-coated lactic acid bacteria according to the present invention have an excellent acid resistance, a bile resistance, and a heat resistance, and have a low moisture content to be stable against moisture. As such, when orally taken, since the lactic acid bacteria are hardly killed by gastric acid or bile acid, inherent physiological activities of the lactic acid bacteria may be maintained for a long time. Accordingly, the multi-coated lactic acid bacteria according to the present invention may be used in various products which require active lactic acid bacteria, for example, fermented milk, processed milk, fermented soybean products, fermented kimchi products, functional drinks, functional foods, conventional foods, medicines, and cosmetics.

BEST MODE FOR CARRYING OUT THE INVENTION

Hereinafter, the present invention will be described in detail by explaining embodiments of the invention with reference to the attached drawings. The following embodiments are provided to gain a sufficient understanding of the present invention and not to limit the scope of the present invention. Matters not provided in the following descriptions can be sufficiently and technically inferred by one of ordinary skill in the art and thus will not be described here.

Comparative Example 1 and 2, and Embodiments 1 and 2

Preparation of Lactic Acid Bacteria Having Multi-Coating Layer

Comparative Example 1

Preparation of Lactic Acid Bacteria Coated with Protein and Polysaccharide

Initially, lactic acid bacteria *lactobacillus acidophilus* (CBT-LH) single-coated with protein were prepared as follows.

Specifically, 4 kg of powdered skim milk and 2 kg of isolated soy protein were suspended in 100 kg of water. In an enzyme treatment tank equipped with a low-speed agitator and temperature and pH regulators, 1.02 g of a protease (DSM, Delvolase) was added and dissolved in 100 Ml of water at 55□ with an initial pH 7.0 and was hydrolyzed to pH 6.0. After the hydrolyzation, 5 kg of glucose, 0.5 kg of yeast extract, 50 g of dipotassium phosphate, 50 g of ammonium citrate, 50 g of sodium acetate, and 10 g of magnesium sulfate were added and dissolved, and the solution was transported to a 200 l anaerobic fermentation tube and was sterilized at 121□ for 15 minutes, was inoculated with 2 l of an inoculum, and was fermented for 12 hours while maintaining pH 6.0 by using ammonia, thereby obtaining a fermented broth. After the fermentation, while the fermented broth was transported to a continuous centrifuge at a flow rate of 60 l/hr, bacteria and protein remnants were settled to prepare a concentrated aqueous solution of lactic acid bacteria. The concentrated aqueous solution of lactic acid bacteria includes *lactobacillus acidophilus* (CBT-LH) single-coated with protein.

After that, a cryoprotectant for freeze-drying the lactic acid bacteria was added into and mixed with the concentrated aqueous solution of lactic acid bacteria. Specifically, 10 l of an aqueous cryoprotectant solution composed of 1 kg of trehalose, 1 kg of mannitol, and 1 kg of maltodextrin was prepared by performing a press and sterilization process, the cryoprotectant was added into the above-prepared concentrated aqueous solution of lactic acid bacteria, and they were stirred in an agitator at a speed of 5,000 RPM to be homogenized. Although freeze-drying of the concentrated aqueous solution of lactic acid bacteria is performed after a multi-coating process is completed, in order to kill lactic acid bacteria and to obtain an appropriate process flow, the cryoprotectant was previously mixed with the concentrated aqueous solution of lactic acid bacteria and then they were homogenized.

Then, *lactobacillus acidophilus* (CBT-LH) double-coated with protein and polysaccharide were prepared as follows. After 3 l of an aqueous polysaccharide solution in which 10 g of xantan gum and 10 g of carboxymethyl cellulose (CMC) were dissolved was prepared by performing a press and sterilization process, the aqueous polysaccharide solution was mixed with the concentrated aqueous solution of lactic acid bacteria coated with protein, and they were stirred in an agitator at a speed of 5,000 RPM to be homogenized, thereby preparing a concentrated aqueous solution of lactic acid bacteria double-coated with protein and polysaccharide.

After that, the concentrated aqueous solution of double-coated lactic acid bacteria was freeze-dried. Specifically, the concentrated aqueous solution of double-coated lactic acid bacteria was homogenized, was rapidly frozen in a freezer at −55□, and then was freeze-dried at 0 to 40□.

Comparative Example 2

Preparation of Lactic Acid Bacteria Coated with Protein, Polysaccharide, and Nanoparticles A triple-coating layer was formed by adding nanoparticles into the lactic acid bacteria-concentrated aqueous solution including protein and polysaccharide (the lactic acid bacteria-concentrated aqueous solution immediately before being freeze-dried), which was prepared in Comparative Example 1, as follows.

Initially, in order to prepare the nanoparticles, stearic acid and soy lecithin were put into a water tank at 70□ to remove alcohol groups and were dissolved to prepare an aqueous phase (W/O type). The aqueous phase was added to an oil phase (O/W type) at high temperature of about 80□ by using a syringe needle, and they were mixed at 70 to 80□ for 2 hours. The prepared modified starch suspension was cooled to room temperature while being re-dispersed for 300 seconds by using an ultrasonic homogenizer, and was passed through a millipore filter to select only nanoparticles of 100 to 200 nm, thereby preparing nanoparticles for triple coating.

2 weight % of the prepared nanoparticles with respect to the weight of the above-prepared concentrated aqueous solution of double-coated lactic acid bacteria (the concentrated aqueous solution including protein and polysaccharide) was measured, and the nanoparticles and the concentrated aqueous solution of lactic acid bacteria were mixed by using a multi-mixer for 10 to 30 minutes, thereby preparing a concentrated aqueous solution of triple-coated lactic acid bacteria to which the nanoparticles were added.

After that, the concentrated aqueous solution of triple-coated lactic acid bacteria was freeze-dried. Specifically, the concentrated aqueous solution of triple-coated lactic acid bacteria was homogenized, was rapidly frozen in a freezer at −55□, and then was freeze-dried at 0 to 40□.

Embodiment 1

Preparation of Lactic Acid Bacteria Multi-Coated with Protein, Polysaccharide, and Edible Oil/Fat In order to prepare the multi-coated lactic acid bacteria according to the present invention, a concentrated aqueous solution of multi-coated lactic acid bacteria was prepared by adding edible oil/fat into the concentrated aqueous solution of lactic acid bacteria double-coated with protein and polysaccharide, which was prepared in Comparative Example 1, as follows.

Initially, the edible oil/fat was emulsified as follows.

50 g of edible beef tallow, 2.5 g of lecithin, and 447.5 g of an aqueous solution were uniformly mixed to be emulsified, thereby preparing edible oil/fat emulsified to a total of 500 g. The above emulsified edible oil/fat was added into the concentrated aqueous solution of double-coated lactic acid bacteria, and they were stirred by using a homogenizer for 5 to 20 minutes at a speed of 5,000 RPM to be uniformly mixed, thereby preparing a concentrated aqueous solution of multi-coated lactic acid bacteria.

After that, in order to increase binding forces of coating agents and to prevent death of the lactic acid bacteria due to moisture, a freeze-drying process for removing moisture was performed as follows. The concentrated aqueous solution of multi-coated lactic acid bacteria was frozen in a freezer at a temperature equal to or less than −55□ for 2 to 4 days, and then was freeze-dried at 0 to 40□ for 2 to 6 days by using a freeze-dryer (IIshin), thereby preparing multi-coated lactic acid bacteria.

Embodiment 2

Preparation of Lactic Acid Bacteria Multi-Coated with Protein, Polysaccharide, Nanoparticles, and Edible Oil/Fat A concentrated aqueous solution of multi-coated lactic acid bacteria was prepared by adding edible oil/fat into the concentrated aqueous solution of lactic acid bacteria triple-coated with protein, polysaccharide, and nanoparticles, which was prepared in Comparative Example 2.

Initially, the edible oil/fat was prepared as in Embodiment 1. The emulsified edible oil/fat was added into the concentrated aqueous solution of triple-coated lactic acid bacteria, and they were stirred by using a homogenizer for 5 to 20 minutes at a speed of 5,000 RPM to be uniformly mixed, thereby preparing a concentrated aqueous solution of multi-coated lactic acid bacteria.

After that, a freeze-drying process was performed as in Embodiment 1, thereby preparing freeze-dried and multi-coated lactic acid bacteria.

Test Example 1

Comparison of Acid Resistances according to Types of Multi-Coated Lactic Acid Bacteria The acid resistances of the lactic acid bacteria prepared in Comparative Examples 1 and 2 and Embodiments 1 and 2 were measured and compared as shown in Table 1.

Specifically, $3.40 \times 10^{11}$ cfu/g of the lactic acid bacteria prepared in Comparative Examples 1 and 2 and Embodiments 1 and 2 were individually treated with artificial gastric juice at pH 2.1 for 30, 60, 90, and 120 minutes. After diluting by using a 10 fold dilution method in a physiological saline solution or a phosphate-buffered diluent and smearing on an agar plate, the number of lactic acid bacteria was counted.

TABLE 1

| Exposure Time (min.) | Embodiment 1 (Test Group) (cfu/g) Multi-coating Coated with Polysaccharide + Oil/Fat | Comparative Example 1 (Control Group) (cfu/g) Double-coating Coated with Polysaccharide | Embodiment 2 (Test Group) (cfu/g) Multi-coating Coated with Polysaccharide + Nanoparticles + Oil/Fat | Comparative Example 2 (Control Group) (cfu/g) Triple-coating Coated with Polysaccharide + Nanoparticles |
|---|---|---|---|---|
| 0 | $3.31 \times 10^{11}$ | $3.41 \times 10^{11}$ | $3.29 \times 10^{11}$ | $3.47 \times 10^{11}$ |
| 30 | $2.98 \times 10^{11}$ | $2.91 \times 10^{11}$ | $3.20 \times 10^{11}$ | $3.21 \times 10^{11}$ |
| 60 | $2.73 \times 10^{11}$ | $2.37 \times 10^{11}$ | $3.05 \times 10^{11}$ | $3.15 \times 10^{11}$ |
| 90 | $2.38 \times 10^{11}$ | $1.88 \times 10^{11}$ | $2.87 \times 10^{11}$ | $3.11 \times 10^{11}$ |
| 120 | $2.28 \times 10^{11}$ | $1.70 \times 10^{11}$ | $2.65 \times 10^{11}$ | $2.10 \times 10^{11}$ |
| Survival Ratio (%) after 120 min. | 68.9% | 49.9% | 80.5% | 60.5% |

As shown in Table 1, the lactic acid bacteria of Embodiments 1 and 2 prepared by using the preparing methods according to the present invention have higher acid resistances than those of the lactic acid bacteria of Comparative Examples 1 and 2. In particular, as time passes, relative acid resistances are further increased.

Test Example 2

Comparison of Bile Resistances According to Types of Multi-Coated Lactic Acid Bacteria The bile resistances of the lactic acid bacteria prepared in Comparative Examples 1 and 2 and Embodiments 1 and 2 were measured and compared as shown in Table 2.

Specifically, $3.50 \times 10^{11}$ cfu/g of the lactic acid bacteria prepared in Comparative Examples 1 and 2 and Embodiments 1 and 2 were individually treated with 0.5% of an oxgall solution for 30, 60, 90, and 120 minutes. After diluting by using a 10 fold dilution method in a physiological saline solution or a phosphate-buffered diluent and smearing on an agar plate, the number of lactic acid bacteria was counted.

Examples 1 and 2. In particular, as time passes, relative bile resistances are further increased.

Test Example 3

Comparison of Accelerated Test Stabilities According to Types of Multi-Coated Lactic Acid Bacteria The accelerated test stabilities of the lactic acid bacteria prepared in Comparative Examples 1 and 2 and Embodiments 1 and 2 were measured and compared as shown in Table 3.

Specifically, $3.20 \times 10^{11}$ cfu/g of the lactic acid bacteria prepared in Comparative Examples 1 and 2 and Embodiments 1 and 2 were maintained at 40□ at a relative humidity of 70%

TABLE 2

| Exposure Time (min.) | Embodiment 1 (Test Group) (cfu/g) Multi-coating Coated with Polysaccharide + Oil/Fat | Comparative Example 1 (Control Group) (cfu/g) Double-coating Coated with Polysaccharide | Embodiment 2 (Test Group) (cfu/g) Multi-coating Coated with Polysaccharide + Nanoparticles + Oil/Fat | Comparative Example 2 (Control Group) (cfu/g) Triple-coating Coated with Polysaccharide + Nanoparticles |
|---|---|---|---|---|
| 0 | $3.33 \times 10^{11}$ | $3.51 \times 10^{11}$ | $3.30 \times 10^{11}$ | $3.60 \times 10^{11}$ |
| 30 | $3.17 \times 10^{11}$ | $2.76 \times 10^{11}$ | $3.15 \times 10^{11}$ | $3.20 \times 10^{11}$ |
| 60 | $2.89 \times 10^{11}$ | $2.25 \times 10^{11}$ | $3.09 \times 10^{11}$ | $2.76 \times 10^{11}$ |
| 90 | $2.53 \times 10^{11}$ | $1.73 \times 10^{11}$ | $2.64 \times 10^{11}$ | $2.31 \times 10^{11}$ |
| 120 | $2.17 \times 10^{11}$ | $1.57 \times 10^{11}$ | $2.53 \times 10^{11}$ | $2.08 \times 10^{11}$ |
| Survival Ratio (%) after 120 min. | 65.2% | 44.7% | 76.7% | 57.8% |

As shown in Table 2, the lactic acid bacteria of Embodiments 1 and 2 prepared by using the preparing methods according to the present invention have higher bile resistances than those of the lactic acid bacteria of Comparative for 10, 20, 30, and 40 days. After diluting by using a 10 fold dilution method in a physiological saline solution or a phosphate-buffered diluent and smearing on an agar plate, the number of lactic acid bacteria was counted.

TABLE 3

| Elapsed Time (days) | Embodiment 1 (Test Group) (cfu/g) Multi-coating Coated with Polysaccharide + Oil/Fat | Comparative Example 1 (Control Group) (cfu/g) Double-coating Coated with Polysaccharide | Embodiment 2 (Test Group) (cfu/g) Multi-coating Coated with Polysaccharide + Nanoparticles + Oil/Fat | Comparative Example 2 (Control Group) (cfu/g) Triple-coating Coated with Polysaccharide + Nanoparticles |
|---|---|---|---|---|
| 0 | $3.39 \times 10^{11}$ | $3.11 \times 10^{11}$ | $3.28 \times 10^{11}$ | $3.22 \times 10^{11}$ |
| 10 | $3.17 \times 10^{11}$ | $3.01 \times 10^{11}$ | $3.09 \times 10^{11}$ | $3.00 \times 10^{11}$ |
| 20 | $2.77 \times 10^{11}$ | $2.56 \times 10^{11}$ | $2.76 \times 10^{11}$ | $2.39 \times 10^{11}$ |
| 30 | $2.56 \times 10^{11}$ | $1.86 \times 10^{11}$ | $2.53 \times 10^{11}$ | $1.88 \times 10^{11}$ |
| 40 | $2.08 \times 10^{11}$ | $1.32 \times 10^{11}$ | $2.38 \times 10^{11}$ | $1.65 \times 10^{11}$ |
| Survival Ratio (%) after 40 days | 61.4% | 42.4% | 72.6% | 51.2% |

As shown in Table 3, the lactic acid bacteria of Embodiments 1 and 2 prepared by using the preparing methods according to the present invention have higher accelerated test stabilities than those of the lactic acid bacteria of Comparative Examples 1 and 2. In particular, as time passes, relative stabilities are further increased. The above result shows that the lactic acid bacteria coated with edible oil/fat in Embodiments 1 and 2 have much higher stabilities against high temperature and humidity in comparison to the lactic acid bacteria not coated with edible oil/fat in Comparative Examples 1 and 2.

Test Example 4

Comparison of Moisture Contents According to Types of Multi-Coated Lactic Acid Bacteria The moisture contents of the lactic acid bacteria prepared in Comparative Examples 1 and 2 and Embodiments 1 and 2 were measured and compared as shown in Table 4.

Specifically, $3.20 \times 10^{11}$ cfu/g of the lactic acid bacteria prepared in Comparative is Examples 1 and 2 and Embodiments 1 and 2 were maintained at 30° C. at a relative humidity of 70% for 3, 6, and 9 hours and 10 days. 5 g of samples were taken in every test time and their moisture contents (%) were measured and moisture variations were checked by using an infrared moisture meter (a heating, drying, and weighing method using infrared which is the closest to a loss on drying method, Kett, Japan).

TABLE 4

| Elapsed Time (days) | Embodiment 1 (Test Group) moisture content (%) Multi-coating Coated with Polysaccharide + Oil/Fat | Comparative Example 1 (Control Group) moisture content (%) Double-coating Coated with Polysaccharide | Embodiment 2 (Test Group) moisture content (%) Multi-coating Coated with Polysaccharide + Nanoparticles + Oil/Fat | Comparative Example 2 (Control Group) moisture content (%) Triple-coating Coated with Polysaccharide + Nanoparticles |
|---|---|---|---|---|
| 0 Hour | 1.860 | 1.730 | 1.534 | 1.589 |
| 3 Hours | 3.397 | 5.278 | 3.025 | 4.897 |
| 6 Hours | 3.496 | 5.485 | 3.127 | 5.056 |
| 9 Hours | 3.364 | 5.245 | 3.117 | 4.928 |
| 10 Days | 2.909 | 4.960 | 2.713 | 4.658 |
| Moisture Variation (%) after 10 days | 156.4% | 286.7% | 176.9% | 293.1% |

As shown in Table 4, the lactic acid bacteria of Embodiments 1 and 2 prepared by using the preparing methods according to the present invention have lower moisture contents than those of the lactic acid bacteria of Comparative Examples 1 and 2. In particular, as time passes, relative moisture contents are further reduced. After 10 days pass, moisture variations in Embodiments 1 and 2 are equal to or less than 50 to 60% of those in Comparative Examples 1 and 2, and their moisture contents are definitely reduced. The above result shows that the lactic acid bacteria coated with edible oil/fat in Embodiments 1 and 2 have much higher stabilities against moisture variations in comparison to the lactic acid bacteria not coated with edible oil/fat in Comparative Examples 1 and 2.

INDUSTRIAL APPLICABILITY

The multi-coated lactic acid bacteria according to the present invention may achieve an improved acid resistance, a high bile resistance, and a high accelerated test stability in an extreme environment, and may have a low moisture content to be particularly stable against a moisture variation. Also, when orally taken, since the multi-coated lactic acid bacteria are not killed by gastric acid or bile acid, inherent physiological activities of the lactic acid bacteria are not lost.

Accordingly, the multi-coated lactic acid bacteria according to the present invention may be appropriately used to prepare fermented milk, processed milk, fermented soybean products, fermented kimchi products, functional drinks, functional foods, conventional foods, cosmetics, etc. which require active lactic acid bacteria.

The invention claimed is:

1. Multi-coated lactic acid bacteria comprising:
   lactic acid bacteria,
   a multi coating layer forming matrix structure comprising a first coating layer comprising protein which is coated on the lactic acid bacteria; a second coating layer comprising polysaccharide which is coated on the first coating layer; a third coating layer comprising nanoparticle which is coated on the second coating layer; and a fourth coating layer comprising edible oil/fat which is coated on the third coating layer and forming matrix structure;
   wherein the edible oil/fat is selected from the group consisting of edible beef tallow, edible pork lard, coconut oil, palm oil, cocoa fat, and mixtures thereof.

2. The multi-coated lactic acid bacteria of claim 1, wherein the multi-coating layer is formed by protease-processing an aqueous protein solution and fermenting lactic acid bacteria in the protease-processed aqueous protein solution so as to prepare a concentrated aqueous solution of lactic acid bacteria, and adding the polysaccharide and edible oil/fat into the concentrated aqueous solution of lactic acid bacteria.

3. The multi-coated lactic acid bacteria of claim 2, wherein the edible oil/fat is emulsified by an edible emulsifier before being added into the concentrated aqueous solution of lactic acid bacteria.

4. The multi-coated lactic acid bacteria of claim 1, wherein the lactic acid bacteria comprise at least one selected from the group consisting of genus *Streptococcus*, genus *Lactococcus*, genus *Enterococcus*, genus *Lactobacillus*, genus *Pediococcus*, genus *Leuconostoc*, genus *Weissella*, and genus *Bifidobacterium*.

5. The multi-coated lactic acid bacteria of claim 1, wherein the protein is formed by adding a sugar for culturing lactic acid bacteria into a protease-processed aqueous protein solution comprising isolated soy protein and powdered skim milk solution, or an aqueous protein solution comprising soy peptone and casein peptone, and fermenting the lactic acid bacteria in the protease-processed aqueous protein solution or the aqueous protein solution.

6. The multi-coated lactic acid bacteria of claim 5, wherein the sugar for culturing lactic acid bacteria comprises 1 to 5 weight % of glucose, 0.1 to 1.5 weight % of yeast extract, and 0.01 to 0.1 weight % of an ionic component with respect to a total weight of the protease-processed aqueous protein solution.

7. The multi-coated lactic acid bacteria of claim 1, wherein the polysaccharide is selected from the group consisting of xantan gum, carboxymethyl cellulose (CMC), levan, and mixtures thereof.

8. The multi-coated lactic acid bacteria of claim 1, wherein the nanoparticle is formed by forming nanoparticles by using a material selected from the group consisting of gelatin, casein, lecithin, dextran, gum acacia, cholesterol, stearic acid, calcium stearate, sorbitan ester, phosphate, cellulose, polyvinylalcohol, and combinations thereof.

9. The multi-coated lactic acid bacteria of claim 2, wherein the multi-coated lactic acid bacteria are in a state of original powder of lactic acid bacteria prepared by adding a cryoprotectant into and then freeze-drying the concentrated aqueous solution of lactic acid bacteria.

10. A product comprising the multi-coated lactic acid bacteria of claim 1.

11. The product of claim 10, wherein the product is selected from the group consisting of fermented milk, processed milk, fermented soybean products, fermented kimchi products, functional drinks, functional foods, conventional foods, medicines, and cosmetics.

\* \* \* \* \*